US010376539B2

(12) United States Patent
Bogin et al.

(10) Patent No.: US 10,376,539 B2
(45) Date of Patent: Aug. 13, 2019

(54) AUGMENTATION OF ANTIINFLAMMATORY, IMMUNOMODULATORY, AND REGENERATIVE PROCESSES IN AMYOTROPHIC LATERAL SCLEROSIS USING XENON AND NOBLE GAS COMBINATIONS

(71) Applicant: NOBLIS THERAPEUTICS, INC., Portland, OR (US)

(72) Inventors: Vlad Bogin, Portland, OR (US); Thomas Ichim, San Diego, CA (US); Santosh Kesari, Santa Monica, CA (US)

(73) Assignee: Nobilis Therapeutics, Inc., Portland, OR (US)

( * ) Notice: Subject to any disclaimer, the term of this patent is extended or adjusted under 35 U.S.C. 154(b) by 0 days.

(21) Appl. No.: 15/598,268

(22) Filed: May 17, 2017

(65) Prior Publication Data

US 2017/0333473 A1 Nov. 23, 2017

Related U.S. Application Data

(60) Provisional application No. 62/337,787, filed on May 17, 2016.

(51) Int. Cl.
*A61K 35/28* (2015.01)
*A61K 33/00* (2006.01)
(Continued)

(52) U.S. Cl.
CPC ............. *A61K 33/00* (2013.01); *A61K 35/28* (2013.01); *A61K 35/51* (2013.01); *A61K 2035/124* (2013.01)

(58) Field of Classification Search
CPC .............................. A61K 35/28; A61K 33/00
See application file for complete search history.

(56) References Cited

U.S. PATENT DOCUMENTS

2007/0178591 A1* 8/2007 Honmou ............ A61K 38/2013
435/365
2017/0095505 A1* 4/2017 Lavaur ................... A61K 9/12

FOREIGN PATENT DOCUMENTS

WO WO-2015177435 A1 * 11/2015 ............... A61K 9/12

OTHER PUBLICATIONS

Johnson et al., "Glutamate receptors as therapeutic targets for Parkinson's Disease," CNS Neurol Discord Drug Targets 8(6):475-491, 2009.*

(Continued)

*Primary Examiner* — Rosanne Kosson
(74) *Attorney, Agent, or Firm* — Marc Baumgartner; Baumgartner Patent Law

(57) ABSTRACT

Disclosed are methods of inhibiting progression, stabilizing and reversing amyotrophic lateral sclerosis and neuromuscular degenerative diseases including spinal muscular atrophy, by administration of xenon, or noble gas compositions at a sufficient frequency and concentration to evoke antiinflammatory, immunomodulatory, and regenerative processes in a patient in need of therapy. In one embodiment, xenon is administered as a pharmaceutical preparation at a concentration of 5 to 90% by volume, more preferably for certain embodiments, at 5 to 30% by volume, wherein said pharmaceutical preparation additionally contains oxygen, argon, nitrogen and/or air. In other embodiments argon is utilized together, or as a replacement for xenon. Furthermore, the use of xenon and/or other noble gas combinations are disclosed for augmentation of therapies that augment endogenous regenerative cells.

7 Claims, 1 Drawing Sheet

Square = Xenon
Diamond = BM Cells
Triangle = BM Cells + Xenon

(51) Int. Cl.
 *A61K 35/51* (2015.01)
 *A61K 35/12* (2015.01)

(56) References Cited

OTHER PUBLICATIONS

Nagastu et al., "Inflammatory process in Parkinson's Disease: role for cytokines," Current Pharmaceutical Design 11:999-1016, 2005.*
Banks et al., "Passage of cytokines across the blood-brain barrier," 2(4):241-248, 1995.*

* cited by examiner

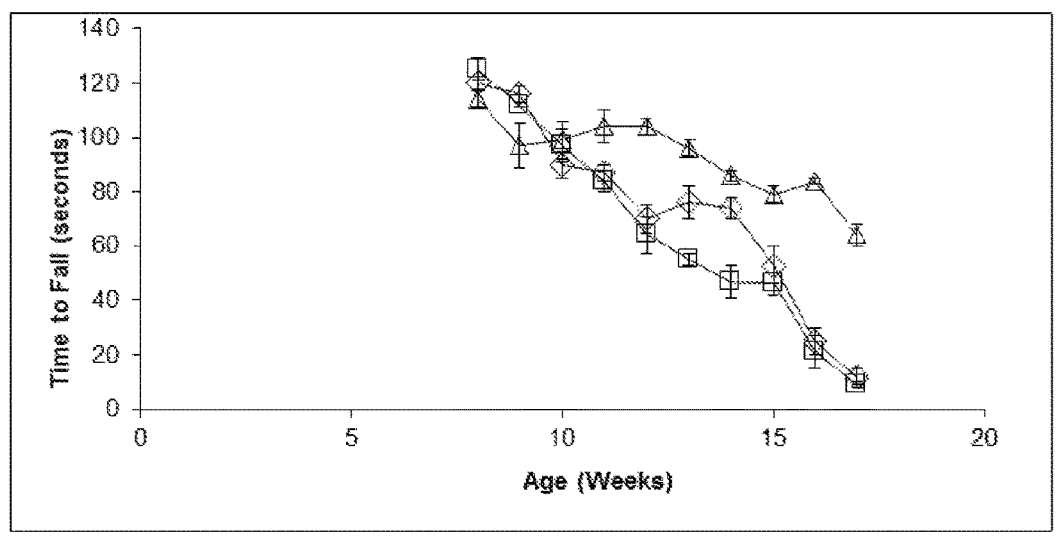
Square = Xenon
Diamond = BM Cells
Triangle = BM Cells + Xenon

AUGMENTATION OF ANTIINFLAMMATORY, IMMUNOMODULATORY, AND REGENERATIVE PROCESSES IN AMYOTROPHIC LATERAL SCLEROSIS USING XENON AND NOBLE GAS COMBINATIONS

CROSS-REFERENCE TO RELATED APPLICATIONS

This application claims priority to U.S. Provisional Application No. 62/337,787, filed May 17, 2016, which is incorporated herein by reference in its entirety.

FIELD OF THE INVENTION

The invention pertains to the field of Noble Gases, more particularly the invention pertains to augmentation of antiinflammatory, immune modulatory, and regenerative activities of known agents using the inert gas Xenon and other compositions containing Noble Gases.

BACKGROUND OF THE INVENTION

Numerous studies have demonstrated xenon and other Noble Gases such as Argon exert anti-inflammatory and neuroprotective effects. Mechanistically this has been associated with inhibition of NMDA receptor, as well as induction of anti-apoptotic genes. The current invention teaches a previously unknown and unexpected synergy between xenon and neuroregenerative interventions.

SUMMARY OF THE INVENTION

Disclosed are methods of inhibiting progression, stabilizing and reversing amyotrophic lateral sclerosis and neuromuscular degenerative diseases including spinal muscular atrophy, by administration of xenon, or noble gas compositions at a sufficient frequency and concentration to evoke anti-inflammatory, immunomodulatory, and regenerative processes in a patient in need of therapy. In one embodiment, xenon is administered as a pharmaceutical preparation at a concentration of 5 to 90% by volume, more preferably for certain embodiments, at 5 to 30% by volume, wherein said pharmaceutical preparation additionally contains oxygen, argon, nitrogen and/or air. In other embodiments argon is utilized together, or as a replacement for xenon. Furthermore, the use of xenon and/or other noble gas combinations are disclosed for augmentation of therapies that augment endogenous regenerative cells.

BRIEF DESCRIPTION OF THE DRAWINGS

FIG. 1 is a line graph showing the time to fall in relation to mouse age with three different administered agents: Xenon, BM cells, and Xenon+BM Cells.

DESCRIPTION OF INVENTION

The invention provides means of augmenting endogenous and exogenous neuroregenerative activity by use of Noble Gases at pharmacological concentrations. In one embodiment the invention provides means of augmenting effects of endogenous regenerative cells by administration of xenon prior to, concurrent with, or subsequent to an intervention that stimulates endogeneous regenerative cells. Many types of interventions that stimulate endogenous regenerative cells are known in the art, these include; a) administration of growth factors [1, 2]; b) administration of electromagnetic fields that stimulate growth factors [3, 4], or directly induce activation of regenerative cells [5, 6]; c) performance of mental exercises [7]; d) initiation of physical exercise programs [8]; and e) deep brain/transcranial stimulation [9]. Regenerative cells involved in neuroregeneration include cells of the dentate gyrus, the subventricular zone and the striatum. In one embodiment of the invention, patients suffering from neurogenerative disorders are treated with xenon containing gas mixtures.

In one embodiment regenerative cells are administered exogenously. Said regenerative cells may be semi-pure populations, such as bone marrow, or adipose stromal vascular fraction, or may be mesenchymal stem cells ("MSC"). The differentiation potential of the mesenchymal stem cells that have been described thus far is limited to cells of mesenchymal origin, including the best characterized mesenchymal stem cell (See Pittenger, et al. Science (1999) 284: 143-147 and U.S. Pat. No. 5,827,740 ($SH2^{+}SH4^{+}CD29^{+}CD44^{+}CD71^{+}CD90^{+}CD106^{+}CD120a^{+}CD124^{+}CD14^{-}CD34^{-}CD45^{-}$)). The invention teaches the use of various mesenchymal stem cells. In one embodiment MSC are generated from umbilical cord tissue. Means of generating umbilical cord tissue MSC have been previously published and are incorporated by reference [10-16]. The term "umbilical tissue derived cells (UTC)" refers, for example, to cells as described in U.S. Pat. Nos. 7,510,873, 7,413,734, 7,524,489, and 7,560,276. Said MSC are administered together with, before, or after administration of xenon-containing gases. In some embodiments, MSC are administered for the purpose of producing growth factors that enhance endogenous stem cells to self renew and or differentiate in order to provide a therapeutic benefit.

Various aspects of the invention relating to the above are enumerated in the following paragraphs:

Aspect 1. A method of ameliorating a neurological condition comprising the steps of: a) performing an intervention that stimulates endogenous regenerative cells; b) administrating a Noble Gas containing composition at a sufficient concentration and frequency to induce a therapeutic synergy with said agent capable of stimulating said endogenous regenerative cells.

Aspect 2. The method of aspect 1, wherein said neurological condition is association with loss of neurons.

Aspect 3. The method of aspect 1, wherein said neurological condition is association with loss of neuronal connections.

Aspect 4. The method of aspect 1, wherein said neurological condition is association with abnormal inter axonal communication.

Aspect 5. The method of aspect 1, wherein said neurological condition is selected from a group comprising of: Acquired Epileptiform Aphasia, ADD, ADHD, AIDS—Neurological Complications, Absence of the Septum Pellucidum, Acute Disseminated Encephalomyelitis, Adrenoleukodystrophy, Agenesis of the Corpus Callosum, Agnosia, Aicardi Syndrome, Alexander Disease, Alpers' Disease, Alternating Hemiplegia, Alzheimer's Disease, Amyotrophic Lateral Sclerosis (ALS), Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Aspartame, Asperger Syndrome, Ataxia Telangiectasia, Ataxia, Attention Deficit-Hyperactivity Disorder, Autism, Autonomic Dysfunction, Back Pain, Barth Syndrome, Batten Disease, Benign Intracranial Hypertension, Bernhardt-Roth Syndrome, Behcet's Disease, Bell's Palsy, Benign Essential Blepharospasm, Benign Focal Amyotrophy, Binswanger's Disease, Blepharospasm, Bloch-Sulzberger Syndrome, Brachial Plexus Birth Injuries, Brachial Plexus Injuries, Bradbury-Eggleston Syndrome, Brain Aneurysm, Brain Injury, Brain and Spinal Tumors, Brown-Sequard Syndrome, Bulbospinal Muscular Atrophy, Canavan Disease, Carpal Tunnel Syndrome, Causalgia, Cavernomas, Cavernous Angioma, Cranial Arteritis, Craniosynostosis, Creutzfeldt-Jakob Disease, Cumulative Trauma Disorders, Cushing's Syndrome, Cytomegalic Inclusion Body Disease (CIBD), Cytomegalovirus Infection, Dancing Eyes-Dancing Feet Syndrome, Dandy-Walker Syndrome, Dawson Disease, De Morsier's Syndrome, Dejerine-Klumpke Palsy, Dementia—Multi-Infarct, Dementia—Subcortical, Dementia With Lewy Bodies, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dystonias, Early Infantile Epileptic Encephalopathy, Empty Sella Syndrome, Encephalitis Lethargica, Encephalitis and Meningitis, Encephaloceles, Encephalopathy, Encephalotrigeminal Angiomatosis, Epilepsy, Erb's Palsy, Erb-Duchenne and Dejerine-Klumpke Palsies, Fabry's Disease, Fahr's Syndrome, Fainting, Familial Dysautonomia, Familial Hemangioma, Familial Idiopathic Basal Ganglia Calcification, Familial Spastic Paralysis, Febrile Seizures, Fisher Syndrome, Floppy Infant Syndrome, Friedreich's Ataxia, Gaucher's Disease, Gerstmann's Syndrome, Gerstmann-Straussler-Scheinker Disease, Giant Cell Arteritis, Giant Cell Inclusion Disease, Globoid Cell Leukodystrophy, Glossopharyngeal Neuralgia, Guillain-Barre Syndrome, HTLV-1 Associated Myelopathy, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster Oticus, Herpes Zoster, Hirayama Syndrome, Holoprosencephaly, Huntington's Disease, Hydranencephaly, Hydrocephalus, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Phytanic Acid Storage Disease, Infantile Refsum Disease, Infantile Spasms, Inflammatory Myopathy, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin syndrome, Klippel Feil Syndrome, Klippel-Trenaunay Syndrome (KTS), Kluver-Bucy Syndrome, Korsakoff's Amnesic Syndrome, Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lissencephaly, Locked-In Syndrome, Lou Gehrig's Disease, Lupus—Neurological Sequelae, Lyme Disease—Neurological Complications, Machado-Joseph Disease, Macrencephaly, Megalencephaly, Melkersson-Rosenthal Syndrome, Meningitis, Menkes Disease, Meralgia Paresthetica, Metachromatic Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Congenital, Myopathy—Thyrotoxic, Myopathy, Myotonia Congenita, Myotonia, Narcolepsy, Neuroacanthocytosis, Neurodegeneration with Brain Iron Accumulation, Neurofibromatosis, Neuroleptic Malignant Syndrome, Neurological Complications Of Lyme Disease, Neurological Complications of AIDS, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy—Hereditary, Neurosarcoidosis, Neurotoxicity, Nevus Cavernosus, Niemann-Pick Disease, O'Sullivan-McLeod Syndrome, Occipital Neuralgia, Occult Spinal Dysraphism Sequence, Ohtahara Syndrome, Olivopontocerebellar Atrophy, Opsoclonus Myoclonus, Orthostatic Hypotension, Overuse Syndrome, Pain—Chronic, Paraneoplastic Syndromes, Paresthesia, Parkinson's Disease, Parmyotonia Congenita, Paroxysmal Choreoathetosis, Paroxysmal Hemicrania, Cavernous Malformation, Central Cervical Cord Syndrome, Central Cord Syndrome, Central Nervous System Lymphoma, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Ischemia, Cerebral Palsy, Cerebro-Oculo-Facio-Skeletal Syndrome, Charcot-Marie-Tooth Disorder, Chiari Malformation, Chorea, Choreoacanthocytosis, Chronic Inflammatory Demyelinating Polyneuropathy (CIDP), Chronic Orthostatic Intolerance, Chronic Pain, Coffin Lowry Syndrome, Coma, including Persistent Vegetative State, Complex Regional Pain Syndrome, Congenital Facial Diplegia, Congenital Myasthenia, Congenital Myopathy, Congenital Vascular Cavernous Malformations, Corticobasal Degeneration, Parry Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Lateral Sclerosis, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Pseudotumor Cerebri, Ramsay Hunt Syndrome Type I, Ramsay Hunt Syndrome Type II, Rasmussen's Encephalitis, Reflex Sympathetic Dystrophy Syndrome, Refsum Disease—Infantile, Refsum Disease, Repetitive Motion Disorders, Repetitive Stress Injuries, Restless Legs Syndrome, Retrovirus-Associated Myelopathy, Rett Syndrome, Reye's Syndrome, Riley-Day Syndrome, SUNCT Headache, Sacral Nerve Root Cysts, Saint Vitus Dance, Salivary Gland Disease, Sandhoff Disease, Schilder's Disease, Schizencephaly, Tarlov Cysts, Tay-Sachs Disease, Temporal Arteritis, Tethered Spinal Cord Syndrome, Thomsen Disease, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury (TBI), Tremor, Trigeminal Neuralgia, Tropical Spastic Paraparesis, Tuberous Sclerosis, Seizure Disorder, Septo-Optic Dysplasia, Shaken Baby Syndrome, Shingles, Shy-Drager Syndrome, Sjogren's Syndrome, Sleep Apnea, Sleeping Sickness, Soto's Syndrome, Spasticity, Spina Bifida, Spinal Cord Infarction, Spinal Cord Injury, Spinal Cord Tumors, Spinal Muscular Atrophy, Spinocerebellar Atrophy, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Vasculitis including Temporal Arteritis, Von Economo's Disease, Von Hippel-Lindau disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, Zellweger Syndrome. See National Institute of Neurological Disorders and Stroke Aspect 6. The method of aspect 1, wherein said intervention that stimulates endogenous regenerative cells is a brain neurotrophic factor administration.

Aspect 7. The method of aspect 6, wherein said intervention that stimulates endogenous regenerative cells is a brain neurotrophic factor is administered as a protein.

Aspect 8. The method of aspect 7, wherein said intervention that stimulates endogenous regenerative cells is a brain neurotrophic factor is administered as a protein.

Aspect 9. The method of aspect 7, wherein said intervention that stimulates endogenous regenerative cells is a brain neurotrophic factor is administered as a gene.

Aspect 10. The method of aspect 7, wherein said intervention that stimulates endogenous regenerative cells is a brain neurotrophic factor is administered as a mRNA.

Aspect 11. The method of aspect 7, wherein said intervention that stimulates endogenous regenerative cells is a brain neurotrophic factor is administered as a stabilized mRNA.

Aspect 12. The method of aspect 11, wherein said stabilized mRNA is achieved by utilizing at least one chemically modified oligonucleotide to substitute the natural oligonucleotide in said mRNA sequence Aspect 13. The method of aspect 12, wherein the isolated mRNA comprises at least one chemically modified nucleotide.

Aspect 14. The method of aspect 13, wherein said chemically modified oligonucleotide is selected from a group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methylpseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine,4-methoxy-pseudoisocytidine, 4-methoxy-1-methyl-pseudoisocytidine,2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

Aspect 15. The method of aspect 1, wherein said intervention that stimulates said endogenous regenerative cells comprises administration of compounds, or genes encoding said compounds, or mRNA encoding said compounds, or chemical analogues of compounds, said compounds selected from a group comprising of: a) valproic acid; b) 5-aza cytidine, c) testosterone; d) estrogen; e) human chorionic gonadotropin; f) lithium or salts thereof; g) erythropoietin; h) G-CSF; i) GM-CSF; j) phenyl butyrate; k) M-CSF; l) HGF; m) IGF; n) FGF-alpha; o) FGF-beta; p) CNTF; q) EGF; r) GDF-11; s) PDGF; t) KGF; u) Jagged; v) delta-1; w) delta-2; and x) delta-3.

Aspect 16. The method of aspect 1, wherein said intervention that stimulates said endogenous regenerative cells comprises administration of compounds that inhibit effects of , or genes encoding said compounds which inhibit effects of, or mRNA encoding said compounds which inhibit effects of, or molecules capable of inducing RNA interference toward compounds, with said compounds inducing inhibition of neuroregeneration.

Aspect 17. The method of aspect 16, where said compounds which inhibit neuroregeneration are selected from a group comprising of: a) NOGO A; b) NgR1; c) p75; d) TROY; e) LINGO1; f) NI-35; g) Myelin-associated glycoprotein; h) OMgp; i) Ephrin B3; j) Semaphorin 4D; k) Semaphorin 3A Aspect 18. The method of aspect 1, wherein said intervention that stimulates said endogenous regenerative cells comprises administration of a stem cell.

Aspect 19. The method of aspect 1, wherein said intervention that stimulates said endogenous regenerative cells comprises administration of a hematopoietic stem cell.

Aspect 20. The method of aspect 1, wherein said intervention that stimulates said endogenous regenerative cells comprises administration of hematopoietic stem cell supernatant.

Aspect 21. The method of aspect 1, wherein said intervention that stimulates said endogenous regenerative cells comprises administration of hematopoietic stem cell exosomes.

Aspect 22. The method of aspect 1, wherein said intervention that stimulates said endogenous regenerative cells comprises administration of a mesenchymal stem cell.

Aspect 23. The method of aspect 1, wherein said intervention that stimulates said endogenous regenerative cells comprises administration of a mesenchymal stem cell supernatant.

Aspect 24. The method of aspect 1, wherein said intervention that stimulates said endogenous regenerative cells comprises administration of a mesenchymal stem cell exosome.

Aspect 25. The method of aspect 1, wherein said intervention that stimulates said endogenous regenerative cells comprises administration of cord blood.

Aspect 26. The method of aspect 22, wherein said tissue derived mesenchymal stem cells are selected from a group comprising of: a) bone marrow; b) perivascular tissue; c) adipose tissue; d) placental tissue; e) amniotic membrane; f) omentum; g) tooth; h) umbilical cord tissue; i) fallopian tube tissue; j) hepatic tissue; k) renal tissue; l) cardiac tissue; m) tonsillar tissue; n) testicular tissue; o) ovarian tissue; p) neuronal tissue; q) auricular tissue; r) colonic tissue; s) submucosal tissue; t) hair follicle tissue; u) pancreatic tissue; v) skeletal muscle tissue; and w) subepithelial umbilical cord tissue.

Aspect 27. The method of aspect 22, wherein said mesenchymal stem cells are isolated from tissues containing cells selected from a group of cells comprising of: endothelial cells, epithelial cells, dermal cells, endodermal cells, mesodermal cells, fibroblasts, osteocytes, chondrocytes, natural killer cells, dendritic cells, hepatic cells, pancreatic cells, stromal cells, salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus luteum cells, granulosa lutein cells, theca lutein cells, juxtaglomerular cell, macula densa cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epididymal principal cells, epididymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, melanocytes, retinal pigmented epithelial cells, oogonia/oocytes, spermatids, spermatocytes, spermatogonium cells, spermatozoa, ovarian follicle cells, Sertoli cells, thymus epithelial cell, and/or interstitial kidney cells.

Aspect 28. The method of aspect 22, wherein said mesenchymal stem cells are plastic adherent.

Aspect 29. The method of aspect 22, wherein said mesenchymal stem cells express a marker selected from a group comprising of: a) CD73; b) CD90; and c) CD105.

Aspect 30. The method of aspect 22, wherein said mesenchymal stem cells lack expression of a marker selected from a group comprising of: a) CD14; b) CD45; and c) CD34.

Aspect 31. The method of aspect 26, wherein said mesenchymal stem cells from umbilical cord tissue express markers selected from a group comprising of; a) oxidized low density lipoprotein receptor 1, b) chemokine receptor ligand 3; and c) granulocyte chemotactic protein.

Aspect 32. The method of aspect 26, wherein said mesenchymal stem cells from umbilical cord tissue do not express markers selected from a group comprising of: a) CD117; b) CD31; c) CD34; and CD45;

Aspect 33. The method of aspect 26, wherein said mesenchymal stem cells from umbilical cord tissue express, relative to a human fibroblast, increased levels of interleukin 8 and reticulon 1

Aspect 34. The method of aspect 26, wherein said mesenchymal stem cells from umbilical cord tissue have the potential to differentiate into cells of at least a skeletal muscle, vascular smooth muscle, pericyte or vascular endothelium phenotype.

Aspect 35. The method of aspect 26, wherein said mesenchymal stem cells from umbilical cord tissue express markers selected from a group comprising of: a) CD10; b) CD13; c) CD44; d) CD73; and e) CD90.

Aspect 36. The method of aspect 26, wherein said umbilical cord tissue mesenchymal stem cell is an isolated umbilical cord tissue cell isolated from umbilical cord tissue substantially free of blood that is capable of self-renewal and expansion in culture, Aspect 37. The method of aspect 36, wherein said umbilical cord tissue mesenchymal stem cells has the potential to differentiate into cells of other phenotypes.

Aspect 38. The method of aspect 37, wherein said other phenotypes comprise: a) osteocytic; b) adipogenic; and c) chondrogenic differentiation.

Aspect 39. The method of aspect 26, wherein said cord tissue derived mesenchymal stem cells can undergo at least 20 doublings in culture.

Aspect 40. The method of aspect 26, wherein said cord tissue derived mesenchymal stem cell maintains a normal karyotype upon passaging Aspect 41. The method of aspect 26, wherein said cord tissue derived mesenchymal stem cell expresses a marker selected from a group of markers comprised of: a) CD10 b) CD13; c) CD44; d) CD73; e) CD90; f) PDGFr-alpha; g) PD-L2; and h) HLA-A,B,C Aspect 42. The method of aspect 26, wherein said cord tissue mesenchymal stem cells does not express one or more markers selected from a group comprising of; a) CD31; b) CD34; c) CD45; d) CD80; e) CD86; f) CD117; g) CD141; h) CD178; i) B7-H2; j) HLA-G and k) HLA-DR,DP,DQ.

Aspect 43. The method of aspect 26, wherein said umbilical cord tissue-derived cell secretes factors selected from a group comprising of: a) MCP-1; b) MIP1beta; c) IL-6; d) IL-8; e) GCP-2; f) HGF; g) KGF; h) FGF; i) HB-EGF; j) BDNF; k) TPO; l) RANTES; and m) TIMP1

Aspect 44. The method of aspect 26, wherein said umbilical cord tissue derived cells express markers selected from a group comprising of: a) TRA1-60; b) TRA1-81; c) SSEA3; d) SSEA4; and e) NANOG.

Aspect 45. The method of aspect 26, wherein said umbilical cord tissue-derived cells are positive for alkaline phosphatase staining.

Aspect 46. The method of aspect 26, wherein said umbilical cord tissue-derived cells are capable of differentiating into one or more lineages selected from a group comprising of; a) ectoderm; b) mesoderm, and; c) endoderm Aspect 47. The method of aspect 26, wherein said bone marrow derived mesenchymal stem cells possess markers selected from a group comprising of: a) CD73; b) CD90; and c) CD105.

Aspect 48. The method of aspect 26, wherein said bone marrow derived mesenchymal stem cells possess markers selected from a group comprising of: a) LFA-3; b) ICAM-1; c) PECAM-1; d) P-selectin; e) L-selectin; f) CD49b/CD29; g) CD49c/CD29; h) CD49d/CD29; i) CD29; j) CD18; k) CD61; l) 6-19; m) thrombomodulin; n) telomerase; o) CD10; p) CD13; and q) integrin beta.

Aspect 49. The method of aspect 26, wherein said bone marrow derived mesenchymal stem cell is a mesenchymal stem cell progenitor cell.

Aspect 50. The method of aspect 48, wherein said mesenchymal progenitor cells are a population of bone marrow mesenchymal stem cells enriched for cells containing STRO-1

Aspect 51. The method of aspect 50, wherein said mesenchymal progenitor cells express both STRO-1 and VCAM-1.

Aspect 52. A method of aspect 50, wherein said STRO-1 expressing cells are negative for at least one marker selected from the group consisting of: a) CBFA-1; b) collagen type II; c) PPAR.gamma2; d) osteopontin; e) osteocalcin; f) parathyroid hormone receptor; g) leptin; h) H-ALBP; i) aggrecan; j) Ki67, and k) glycophorin A.

Aspect 53. The method of aspect 26, wherein said bone marrow mesenchymal stem cells lack expression of CD14, CD34, and CD45.

Aspect 54. The method of aspect 52, wherein said STRO-1 expressing cells are positive for a marker selected from a group comprising of: a) VACM-1; b) TKY-1; c) CD146 and; d) STRO-2

Aspect 55. The method of aspect 26, wherein said bone marrow mesenchymal stem cell express markers selected from a group comprising of: a) CD13; b) CD34; c) CD56 and; d) CD117

Aspect 56. The method of aspect 55, wherein said bone marrow mesenchymal stem cells do not express CD10.

Aspect 57. The method of aspect 55, wherein said bone marrow mesenchymal stem cells do not express CD2, CDS, CD14, CD19, CD33, CD45, and DRII.

Aspect 58. The method of aspect 55, wherein said bone marrow mesenchymal stem cells express CD13,CD34, CD56, CD90, CD117 and nestin, and which do not express CD2, CD3, CD10, CD14, CD16, CD31, CD33, CD45 and CD64.

Aspect 59. The method of aspect 26, wherein said skeletal muscle stem cells express markers selected from a group comprising of: a) CD13; b) CD34; c) CD56 and; d) CD117

Aspect 60. The method of aspect 59, wherein said skeletal muscle mesenchymal stem cells do not express CD10.

Aspect 61. The method of aspect 60, wherein said skeletal muscle mesenchymal stem cells do not express CD2, CDS, CD14, CD19, CD33, CD45, and DRII.

Aspect 62. The method of aspect 60, wherein said bone marrow mesenchymal stem cells express CD13,CD34, CD56, CD90, CD117 and nestin, and which do not express CD2, CD3, CD10, CD14, CD16, CD31, CD33, CD45 and CD64.

Aspect 63. The method of aspect 26, wherein said sub-epithelial umbilical cord derived mesenchymal stem cells possess markers selected from a group comprising of; a) CD29; b) CD73; c) CD90; d) CD166; e) SSEA4; f) CD9; g) CD44; h) CD146; and i) CD105

Aspect 64. The method of aspect 63, wherein said sub-epithelial umbilical cord derived mesenchymal stem cells do not express markers selected from a group comprising of; a)CD45; b) CD34; c) CD14; d) CD79; e) CD106; f) CD86; g) CD80; h) CD19; i) CD117; j) Stro-1 and k) HLA-DR.

Aspect 65. The method of aspect 63, wherein said sub-epithelial umbilical cord derived mesenchymal stem cells express CD29, CD73, CD90, CD166, SSEA4, CD9, CD44, CD146, and CD105.

Aspect 66. The method of aspect 63, wherein said sub-epithelial umbilical cord derived mesenchymal stem cells do not express CD45, CD34, CD14, CD79, CD106, CD86, CD80, CD19, CD117, Stro-1, and HLA-DR.

Aspect 67. The method of aspect 63, wherein said sub-epithelial umbilical cord derived mesenchymal stem cells are positive for SOX2.

Aspect 68. The method of aspect 63, wherein said sub-epithelial umbilical cord derived mesenchymal stem cells are positive for OCT4.

Aspect 69. The method of aspect 63, wherein said sub-epithelial umbilical cord derived mesenchymal stem cells are positive for OCT4 and SOX2.

Aspect 70. The method of aspect 1, wherein said xenon is administered to said patient as a pharmaceutical preparation contains 5 to 90% by volume said xenon gas.

Aspect 71. The method of aspect 70 wherein said pharmaceutical preparation contains 5 to 30% by volume of xenon.

Aspect 72. The method of aspect 70 wherein the pharmaceutical preparation additionally contains oxygen, nitrogen and/or air.

Aspect 73. The method aspect 70 wherein the pharmaceutical preparation additionally contains helium, NO, CO, $CO_2$, nitric oxide, argon, or other gaseous compounds and/or inhalable medicaments.

Aspect 74. The method of aspect 70, wherein said pharmaceutical preparation has a ratio of xenon to oxygen of 80 to 20% by volume.

Aspect 75. The method of aspect 70, wherein said pharmaceutical is prepared as a pharmaceutical preparation by mixing xenon with another gas harmless to humans.

Aspect 76. The method of aspect 75 wherein xenon is mixed with an oxygen-containing gas.

Aspect 77. The method of aspect 70, wherein the xenon to oxygen ratio is 80 to 20% by volume.

Aspect 78. The method of aspect 70, wherein said which additionally contains argon at a concentration of 7-25%.

Aspect 79. The method of aspect 1, wherein said noble gas containing composition comprises xenon gas.

Aspect 80. The method of any of aspect 79, wherein the xenon gas is administered at a concentration of 10% to 35% by volume in 21% by volume oxygen gas and a balance of nitrogen gas.

Aspect 81. The method of any of aspect 79 wherein the xenon gas is administered by inhalation, intraocularly, intrathecally, or intranasally.

Aspect 82. The method of aspects 79 wherein the xenon composition comprises a nanoparticle or nanosponge.

Aspect 83. The method of aspect 82, wherein the nanoparticle or nanosponge is administered intravenously, intraarterially, intramuscularly, subcutaneously, intranasally, or intracranially.

Aspect 84. The method of aspect 1, where said noble gas containing mixture of aspect 1, wherein said oxygen is in the range of from about 19% to about 25% by volume of the total composition.

Aspect 85. The method of aspect 1, wherein said noble gas is in the range of from about 19% to about 25% by volume of the total composition.

Aspect 86. The method of aspect 1, wherein said neurological condition is identified by enhanced plasma levels of cytokines associated with inflammation.

Aspect 87. The method of aspect 2, wherein said enhanced neuroinflammation is identified by reduced plasma levels of cytokines associated with anti-inflammation.

EXAMPLE

B6SJL-Tg(SOD1-G93A)1Gur ($SOD1^{G93A}$), which carries the mutant allele human SOD1 containing the Gly 93→Ala substitution. The colony was maintained by crossing transgenic male founders with wild-type female mice at the controlled animal facility. The number of human SOD1 transgenic copies was assessed as described in the Jackson Laboratory manual (https://www.jax.org/strain/002726#jump-nav-5). Bone marrow was obtained from the femur and tibia of adult B6SJL (syngeneic non-ALS mice) of both genders. BMMC were isolated by density gradient (Histopaque 1083; Sigma, St. Louis, Mo., USA) and washed three times with phosphate-buffered saline (PBS). Cells were suspended in saline (250,000 cells/μl) and injected into the lumbar portion of the spinal cord as described in the next section.

$SOD1^{G93A}$ animals were injected with BMMC or vehicle (saline) at 9 or 14 weeks old. Mice were anesthetized with xylazine (15 mg/kg; Vetbrands and ketamine (150 mg/kg; Vetbrands) (Goiânia., GO, Brazil)) intraperitoneally, The animals were immobilized and the spine was exposed. The vertebrae were carefully separated using two fine tweezers in order to reveal the lumbar spinal cord (L4-L5). The BMMC ($10^6$ cells) or saline were injected intraparenchymally with a glass micropipette connected to the nanoinjector (Nanoinject II; Drummond Scientific Company, Broomall, Pa., USA) at the rate of 1 μl minute for a total volume of 4 μl. After recovery from anesthesia, the animals from both groups were returned to the animal facility and kept in cages with food and water ad libitum. 25% xenon was administered every day for a period of 10 minutes in the xenon group.

Functional tests were performed weekly in all experimental groups by blinded investigators. The tests performed was hanging wire test. The animals were placed on the wire lid from their housing cage, where they remained upside down until they fell (maximum time 90 seconds). The longest period that the animal remained in the hanging-wire test was recorded after three trials. Xenon was administered twice weekly at a concentration of 30% in air reconstituted with oxygen for 1 hour per exposure. Results are shown in FIG. 1.

REFERENCES

1. Belayev L, Khoutorova L, Zhao K L, Davidoff A W, Moore A F, Cramer S C. A novel neurotrophic therapeutic strategy for experimental stroke. *Brain research* 1280 117-123 (2009).

2. Zhang W, Sun B, Yu Z, An J, Liu Q, Ren T. High dose erythropoietin promotes functional recovery of rats following facial nerve crush. *Journal of clinical neuroscience: official journal of the Neurosurgical Society of Australasia* 16(4), 554-556 (2009).

3. Li F, Lei T, Xie K et al. Effects of extremely low frequency pulsed magnetic fields on diabetic nephropathy in streptozotocin-treated rats. *Biomedical engineering online* 15 8 (2016).

4. Li R L, Huang J J, Shi Y Q et al. Pulsed electromagnetic field improves postnatal neovascularization in response to hindlimb ischemia. *American journal of translational research* 7(3), 430-444 (2015).

5. Cheng Y, Dai Y, Zhu X et al. Extremely low-frequency electromagnetic fields enhance the proliferation and differentiation of neural progenitor cells cultured from ischemic brains. *Neuroreport* 26(15), 896-902 (2015).

6. Cuccurazzu B, Leone L, Podda MV et al. Exposure to extremely low-frequency (50 Hz) electromagnetic fields enhances adult hippocampal neurogenesis in C57BL/6 mice. *Experimental neurology* 226(1), 173-182 (2010).

7. Veena J, Srikumar B N, Raju T R, Shankaranarayana Rao B S. Exposure to enriched environment restores the survival and differentiation of new born cells in the hippocampus and ameliorates depressive symptoms in chronically stressed rats. *Neuroscience letters* 455(3), 178-182 (2009).

8. Castilla-Ortega E, Rosell-Valle C, Pedraza C, Rodriguez De Fonseca F, Estivill-Torrus G, Santin L J. Voluntary exercise followed by chronic stress strikingly increases mature adult-born hippocampal neurons and prevents stress-induced deficits in 'what-when-where' memory. *Neurobiology of learning and memory* 109 62-73 (2014).

9. Wang H N, Wang L, Zhang R G et al. Anti-depressive mechanism of repetitive transcranial magnetic stimulation in rat: the role of the endocannabinoid system. *Journal of psychiatric research* 51 79-87 (2014).

10. Van Pham P, Truong N C, Le PT et al. Isolation and proliferation of umbilical cord tissue derived mesenchymal stem cells for clinical applications. *Cell and tissue banking* doi:10.1007/s10561-015-9541-6 (2015).

11. Fazzina R, Mariotti A, Procoli A et al. A new standardized clinical-grade protocol for banking human umbilical cord tissue cells. *Transfusion* 55(12), 2864-2873 (2015).

12. Bieback K. Platelet lysate as replacement for fetal bovine serum in mesenchymal stromal cell cultures. *Transfusion medicine and hemotherapy: offizielles Organ der Deutschen Gesellschaft fur Transfusionsmedizin und Immunhamatologie* 40(5), 326-335 (2013).

13. Stanko P, Kaiserova K, Altanerova V, Altaner C. Comparison of human mesenchymal stem cells derived from dental pulp, bone marrow, adipose tissue, and umbilical cord tissue by gene expression. *Biomedical papers of the Medical Faculty of the University Palacky, Olomouc, Czechoslovakia* 158(3), 373-377 (2014).

14. Schira J, Gasis M, Estrada V et al. Significant clinical, neuropathological and behavioural recovery from acute spinal cord trauma by transplantation of a well-defined somatic stem cell from human umbilical cord blood. *Brain: a journal of neurology* 135(Pt 2), 431-446 (2012).

15. Hartmann I, Hollweck T, Haffner S et al. Umbilical cord tissue-derived mesenchymal stem cells grow best under GMP-compliant culture conditions and maintain their phenotypic and functional properties. *Journal of immunological methods* 363(1), 80-89 (2010).

16. Friedman R, Betancur M, Boissel L, Tuncer H, Cetrulo C, Klingemann H. Umbilical cord mesenchymal stem cells: adjuvants for human cell transplantation. *Biology of blood and marrow transplantation: journal of the American Society for Blood and Marrow Transplantation* 13(12), 1477-1486 (2007).

The invention claimed is:

1. A method of ameliorating a neurological condition in a subject in need thereof, wherein the neurological condition is amyotrophic lateral sclerosis (ALS), comprising the steps of:
  a) identifying a subject suffering from the neurological condition;
  b) performing an intervention by administering a therapeutically effective amount of bone marrow mononuclear stem cells (BMMCs) that stimulate endogenous regenerative cells in said subject; and
  c) administrating a gas composition comprising a therapeutically effective concentration of a xenon gas with sufficient frequency to improve the effect of said BMMCs that stimulate said endogenous regenerative cells.

2. The method of claim 1, wherein wherein the gas composition contains 5 to 90% xenon by volume.

3. The method claim 2, wherein said gas composition contains 5 to 30% by volume of xenon.

4. The method of claim 2, wherein the gas composition additionally contains oxygen, nitrogen and/or air.

5. The method of claim 4, wherein said gas composition has a ratio of xenon to air, or xenon to oxygen, of 70% to 30% by volume.

6. The method of claim 1, wherein said neurological condition is identified by enhanced plasma levels of cytokines associated with inflammation.

7. The method of claim 5, wherein the BSCCs are administered to the subject intraparenchymally.

* * * * *